US012636032B2

(12) United States Patent
Schneider et al.

(10) Patent No.: US 12,636,032 B2
(45) Date of Patent: May 26, 2026

(54) MEDICAL INSTRUMENT

(71) Applicant: KARL STORZ SE & Co. KG,
Tuttlingen (DE)

(72) Inventors: Janosz Schneider, Donaueschingen
(DE); Daniel Kärcher, Tuttlingen (DE);
Robin Merz, Tuttlingen (DE); **Sven
Schneider, Tuttlingen (DE); Tobias
Unger, Tuttlingen (DE); Dominik
Längle, Mühlheim-Stetten (DE); Judith
Pönisch**, Tuttlingen (DE)

(73) Assignee: KARL STORZ SE & CO. KG,
Tuttlingen (DE)

( * ) Notice: Subject to any disclaimer, the term of this
patent is extended or adjusted under 35
U.S.C. 154(b) by 38 days.

(21) Appl. No.: 18/722,687

(22) PCT Filed: Dec. 21, 2022

(86) PCT No.: PCT/EP2022/087254
§ 371 (c)(1),
(2) Date: Jun. 21, 2024

(87) PCT Pub. No.: WO2023/118308
PCT Pub. Date: Jun. 29, 2023

(65) Prior Publication Data
US 2025/0057558 A1      Feb. 20, 2025

(30) Foreign Application Priority Data

Dec. 22, 2021    (DE) ..................... 10 2021 134 277.5

(51) Int. Cl.
*A61B 17/00*      (2006.01)
*A61B 17/29*      (2006.01)
*A61B 90/00*      (2016.01)

(52) U.S. Cl.
CPC .......... *A61B 17/2909* (2013.01); *A61B 90/03*
(2016.02); *A61B 90/08* (2016.02);
(Continued)

(58) Field of Classification Search
CPC .. A61B 2017/0046; A61B 2017/00477; A61B
2017/2931; A61B 2017/00862;
(Continued)

(56) References Cited

U.S. PATENT DOCUMENTS

2004/0133235 A1    7/2004  Bacher
2012/0116388 A1*  5/2012  Houser ............ A61B 17/00234
606/1
(Continued)

*Primary Examiner* — Majid Jamialahmadi
(74) *Attorney, Agent, or Firm* — McGlew and Tuttle, P.C.

(57) ABSTRACT

A medical instrument (1) includes a hollow rod (2), at the
distal end (3) of which a tool carrier (4) can be secured by
a first fastening mechanism (5), and the proximal end (6) of
which can be secured to an operating unit (8) by a second
fastening mechanism (7). In order to create a medical
instrument (1) of which the fastening mechanism (5, 7) for
the detachable rod connections is easy to handle during
manufacture and assembly while ensuring a secure hold, it
is proposed that at least the first fastening mechanism (5) for
connecting the tool carrier (4) to the distal end (3) of the rod
(2) is configured as a mechanical latching connection having
at least one resilient element.

19 Claims, 5 Drawing Sheets

(52) U.S. Cl.
CPC ............... *A61B 2017/00477* (2013.01); *A61B 2017/00862* (2013.01); *A61B 2017/292* (2013.01); *A61B 2090/035* (2016.02); *A61B 2090/0808* (2016.02)

(58) Field of Classification Search
CPC .......... A61B 17/29; A61B 2017/00473; A61B 2017/2901; A61B 2017/292; A61B 17/2909; B25G 3/18; B25G 3/12
See application file for complete search history.

(56)                     References Cited

U.S. PATENT DOCUMENTS

| | | |
|---|---|---|
| 2012/0259325 A1 | 10/2012 | Houser et al. |
| 2013/0138129 A1* | 5/2013 | Garrison ............ A61B 18/1445 74/100.1 |
| 2017/0360462 A1 | 12/2017 | Garrison et al. |
| 2021/0275203 A1 | 9/2021 | Malkowski |

\* cited by examiner

MEDICAL INSTRUMENT

CROSS REFERENCE TO RELATED APPLICATIONS

This application is a United States National Phase Application of International Application PCT/EP2022/087254, filed Dec. 21, 2022, and claims the benefit of priority under 35 U.S.C. § 119 of German Application 10 2021 134 277.5, filed Dec. 22, 2021, the entire contents of which are incorporated herein by reference.

TECHNICAL FIELD

The invention relates to a medical instrument comprising a hollow rod, at the distal end of which a tool carrier can be secured by means of a first fastening mechanism, and the proximal end of which can be secured to an operating unit by means of a second fastening mechanism.

BACKGROUND

In order to be able to use the medical instruments in as many different ways as possible, it is known in practice to provide the hollow rod, which is usually designed as a cylindrical rod tube, with a fastening mechanism on the distal and proximal sides in order to be able to connect different tool carriers and/or operating units to the rod.

The instrument systems that can be disassembled into multiple parts known in practice are designed in such a way that at least the fastening mechanism for connecting the tool carrier to the distal end of the rod is designed as a bayonet coupling. To prevent the bayonet coupling from coming loose again due to counter-rotation of the connected components, a special anti-rotation lock is required.

These bayonet couplings have proven themselves in practice, but their manufacture and assembly is very complex, particularly due to the required anti-rotation lock.

SUMMARY

On this basis, the object of the invention is to create a medical instrument, the fastening mechanism of which for the detachable rod connections is easy to handle during manufacture and assembly while ensuring a secure hold.

According to the invention, the solution to this problem is characterized in that at least the first fastening mechanism for connecting the tool carrier to the distal end of the rod is configured as a mechanical latching connection having at least one resilient element.

Mechanical latching connections are characterized by the fact that they have a simple design and are easy to handle, on the one hand, while ensuring a secure connection of the components coupled together in this way, on the other. The resilient element of the latching connection ensures both easy latching and simple and generally tool-free release of the latch.

In a preferred embodiment of the invention, it is proposed that not only the first fastening mechanism for connecting the tool carrier to the distal end of the rod, but also the second fastening mechanism for connecting the proximal end of the rod to the operating unit is configured as a mechanical latching connection having at least one resilient element. The design of the double-sided fastening mechanisms at the distal and proximal ends of the rod enables maximum flexibility for the medical instrument equipped in this way, with simple manufacture.

In order to form the mechanical latching connection, according to a practical embodiment of the invention, it is proposed that the mechanical latching connection comprises at least one latching hook, formed on one of the components to be connected to one another, and at least one corresponding latching receptacle, formed on the other component, for the at least one latching hook, wherein the at least one latching hook is preferably arranged at the free end of a resilient spring tongue. The arrangement of the latching hook on a resilient spring tongue ensures easy actuation of the latch, because the cut-free spring tongue can be deflected without applying great force.

According to the invention, the at least one latching receptacle for receiving the latching hook is advantageously configured as an undercut. The undercut to be engaged by a latching hook represents a latching receptacle that is particularly easy to manufacture, but at the same time ensures a secure and positionally stable latching with the latching hook.

In order to ensure that the latch is held securely and, in particular, to prevent accidental release of the latch, it is proposed according to the invention that a plurality of latching hooks and latching receptacles are arranged distributed around the circumference of the components to be connected to one another.

According to the invention, the latch is released by applying a radially acting compressive force to the latching connection, preferably without tools.

According to a first embodiment for forming the mechanical latching connection, it is proposed that the mechanical latching connection is configured as a plug-in connection that can be executed in the longitudinal direction of the rod. The purely axial stacking of the components to be joined together is a particularly easy and quick to handle design.

In an alternative second embodiment of the mechanical latching connection, it is proposed that the mechanical latching connection is configured as a rotary plug-in connection.

To release the latch, it is proposed according to the invention that a cut-free spring tongue is formed on the component with the latching receptacle in the region of the latch, which tongue can be pressed radially inward to release the latching connection. This cut-free spring tongue allows the radial compressive force required for release to be applied to the latch in a simple and targeted manner. If the medical instrument according to the invention is configured as an HF instrument, the invention further proposes that the cut-free spring tongue can be covered with a tubular cover for insulation purposes.

In order to prevent the components coupled to one another via the mechanical latching connection from twisting, it is further proposed according to the invention that the spring tongue of the latching hook positively abuts against a shoulder of the latching receptacle so as to produce an anti-rotation lock. This anti-rotation lock according to the invention is characterized by the fact that no additional component is required, as is known from the prior art, because the spring tongue automatically positively abuts against the shoulder of the latching receptacle when it is moved into the latching position.

According to a practical embodiment of the invention, the disengagement of the latch of the first fastening mechanism between the tool carrier and the distal end of the rod can be achieved by transferring a tool of the tool carrier to an unlocking position. If the tool is configured with at least one pivoting jaw part, this unlocking position of the tool can, for example, be an over-open position, which can be set exclusively to release the latch.

Finally, in order to facilitate the joining of the components to be coupled together and to align them in the correct position relative to one another, the invention proposes that guide pins are formed on the end sides facing one another of the components to be joined together in order to place the components in the correct position relative to one another.

Further features and advantages of the invention are apparent from the accompanying drawings, in which various exemplary embodiments of a medical instrument according to the invention are shown by way of example only, without limiting the invention to these exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
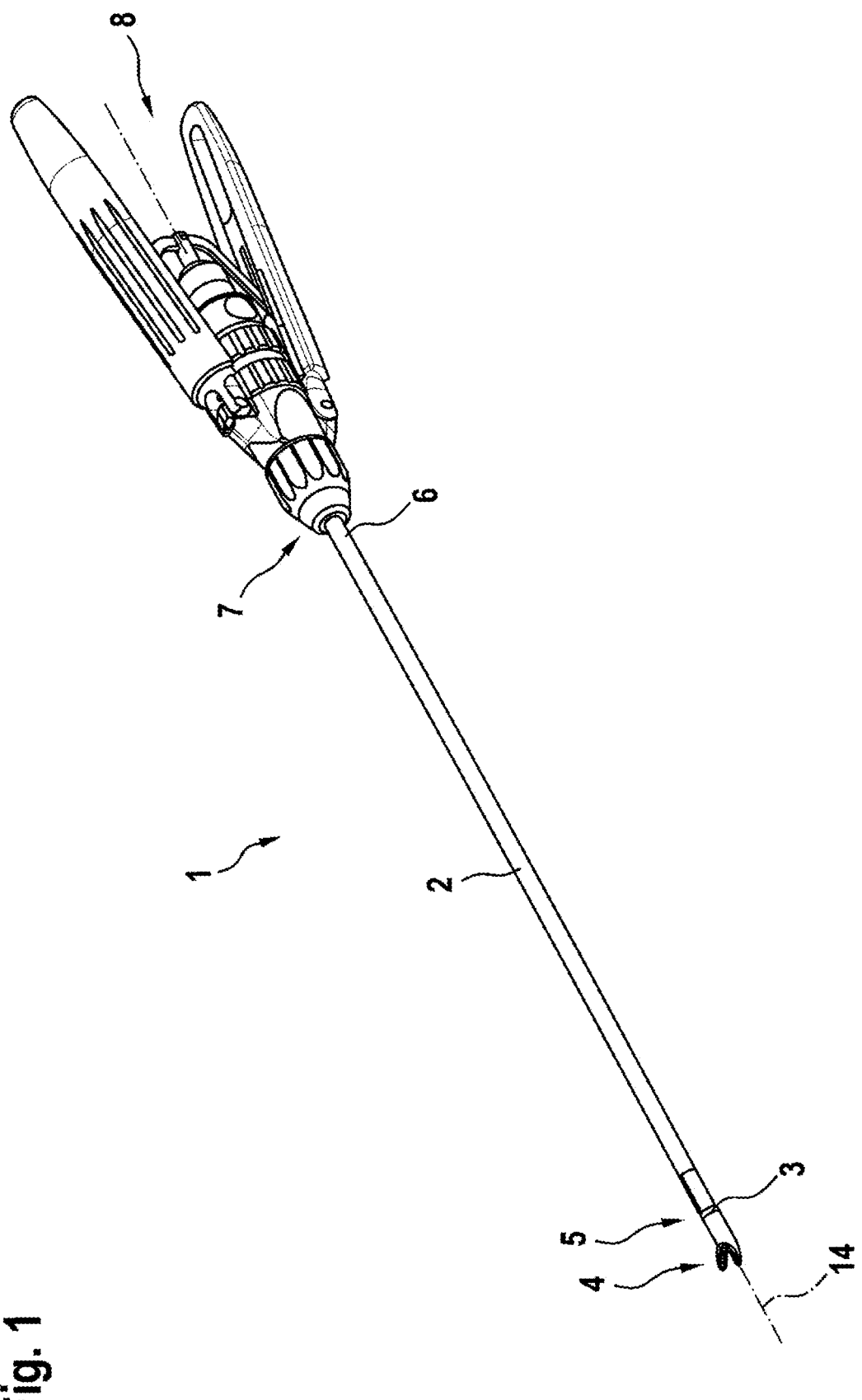
FIG. 1 is a perspective view of a medical instrument according to the invention.

Referring to the drawings, FIG. 1 illustration shows the distal part of a medical instrument 1 with a hollow rod 2, at the distal end 3 of which a tool carrier 4 can be secured by means of a first fastening mechanism 5.

The proximal end 6 of the rod 2 can be secured to an operating unit 8 by means of a second fastening mechanism 7, wherein the operating unit 8 can be a manually operated handle, as shown in FIG. 1, or else an operating unit 8 as used in robot-assisted endoscopy.

In order to make the medical instrument 1 as versatile as possible, the hollow rod 2, which is configured as a cylindrical rod tube, is provided with fastening mechanisms 5 and 7, respectively, at its distal end 3 and at its proximal end 6 in order to be able to connect various tool carriers 4 and/or operating units 8 to the rod 2.

Figure 2:
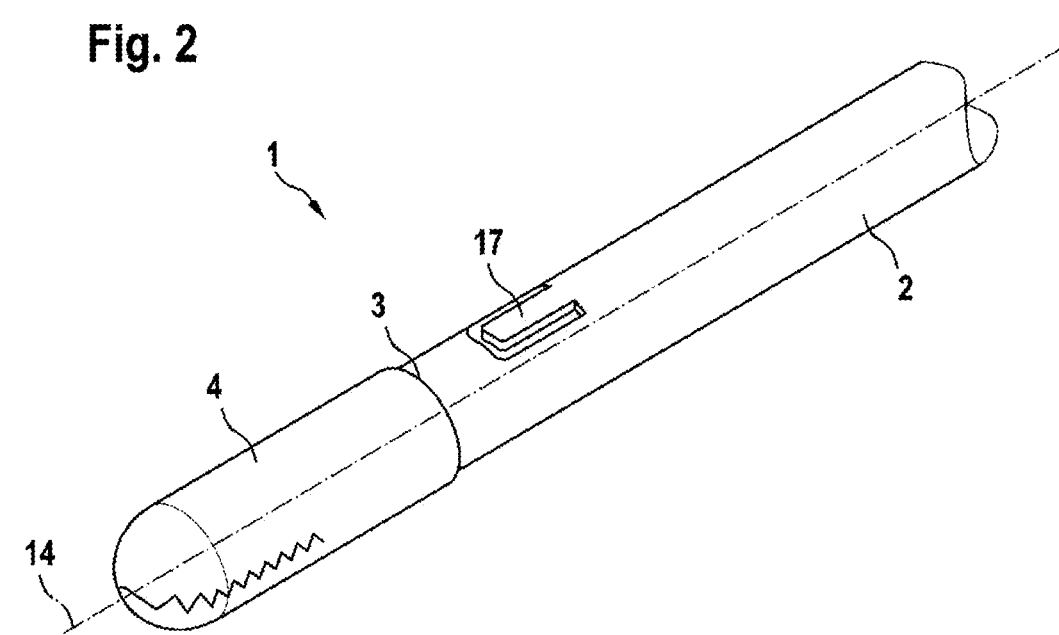
FIG. 2 is a sectional perspective view of the distal end of a first embodiment of a medical instrument according to the invention with a tool carrier fixed to the rod.

FIG. 2 shows the distal end of the medical instrument 1 with a tool carrier 4 fixed to the distal end 3 of the rod 2.

Figure 3:
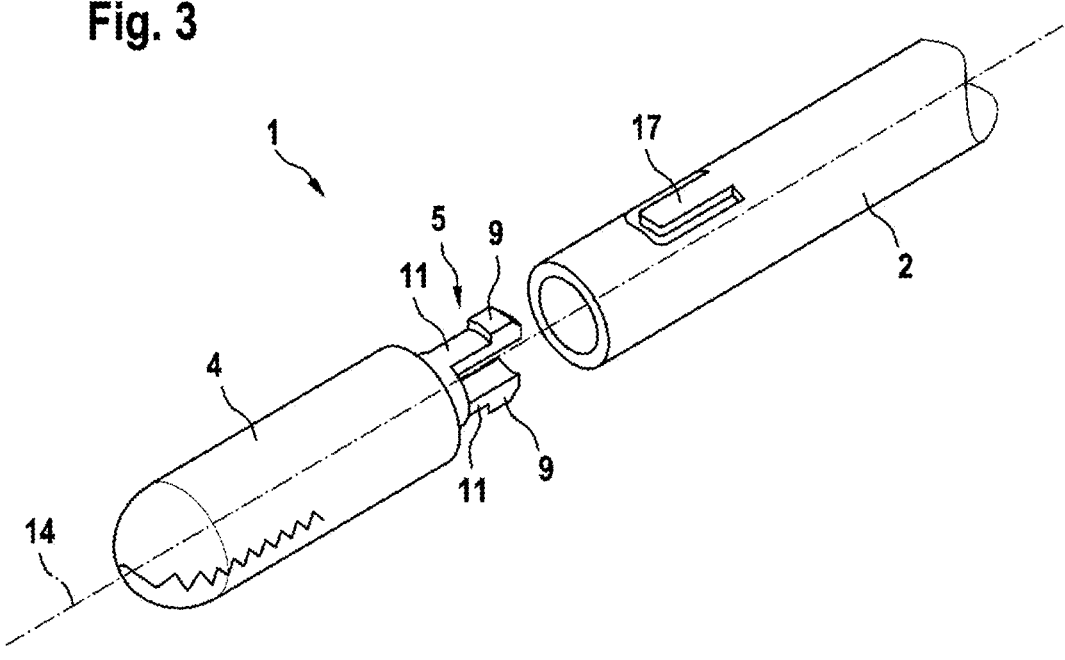
FIG. 3 is a sectional perspective view according to FIG. 2, but showing the tool carrier and the rod in the decoupled state.

The FIG. 3 illustration shows the medical instrument 1 shown in FIG. 2 in a decoupled state, in which the tool carrier 4 is disconnected from the distal end 3 of the rod 2. It can be seen from this illustration that the first fastening mechanism 5 for connecting the tool carrier 4 to the distal end 3 of the rod 2 is configured as a mechanical latching connection.

Even though only the structure of the first fastening mechanism 5 for connecting the tool carrier 4 to the distal end 3 of the rod 2 is shown below with reference to FIGS. 2 to 10, the second fastening mechanism 7 for connecting the proximal end 6 of the rod 2 to the operating unit 8 can also be formed as an identically structured mechanical latching connection.

The structure of the first fastening mechanism 5, which is configured as a mechanical latching connection, can be seen in the illustrations of FIGS. 2 to 6 collectively.

In the first embodiment shown in FIGS. 2 to 6 for forming the mechanical latching connection, the mechanical latching connection comprises at least one latching hook 9 formed on the tool carrier 4 and at least one corresponding latching receptacle 10 formed on the rod 2 for the at least one latching hook 9. As can also be seen from the figures, the at least one latching hook 9 is arranged at the free end of a resilient spring tongue 11 and the at least one latching receptacle 10 for the latching hook 9 is formed as an undercut 12.

Mechanical latching connections are characterized by the fact that they have a simple design and are easy to handle, on the one hand, while ensuring a secure connection of the components coupled together in this way, on the other. The resilient spring tongue 11 of the latching connection ensures both easy latching and simple and generally tool-free release of the latch.

Figure 4:
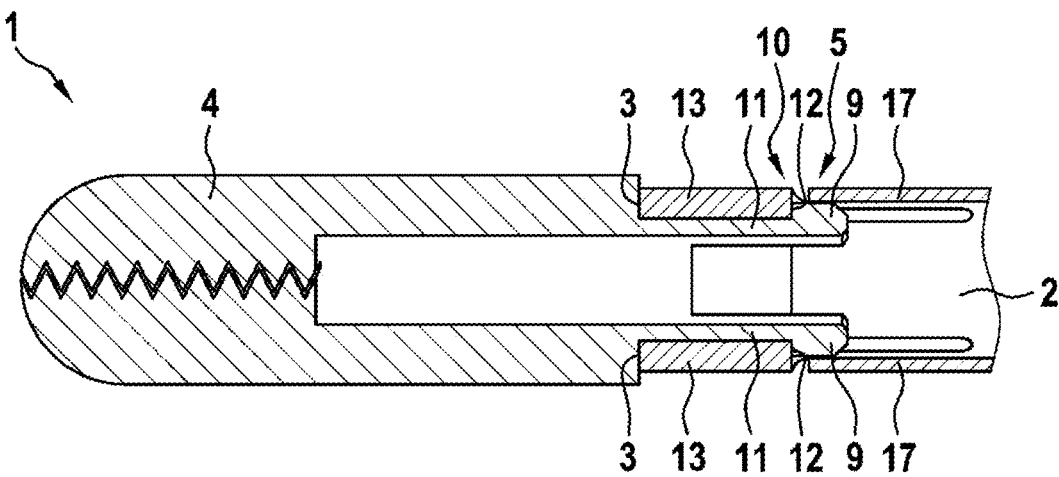
FIG. 4 is a schematic longitudinal sectional view through the illustration according to FIG. 2.
Figure 5:
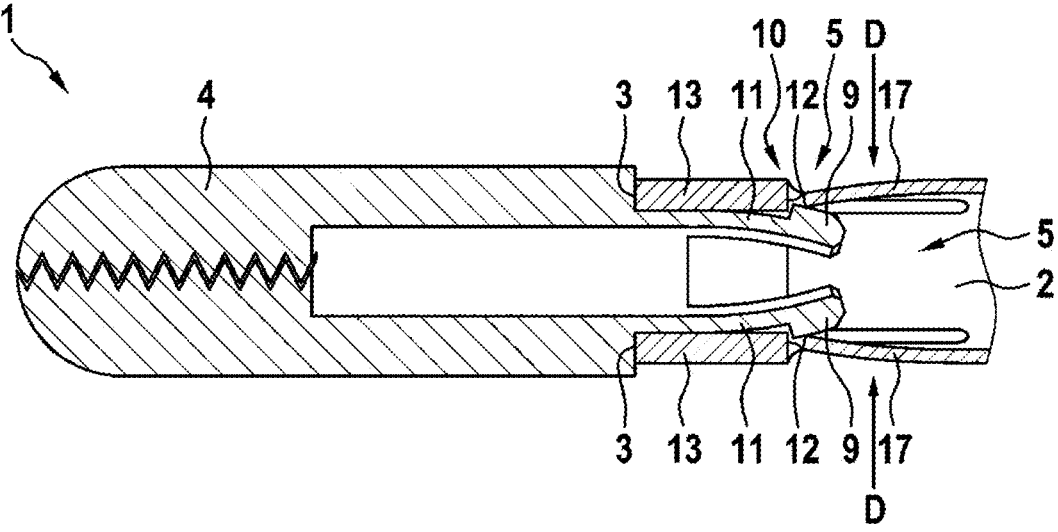
FIG. 5 is a schematic longitudinal sectional view according to FIG. 4, but showing the latch in a release position.
Figure 6:
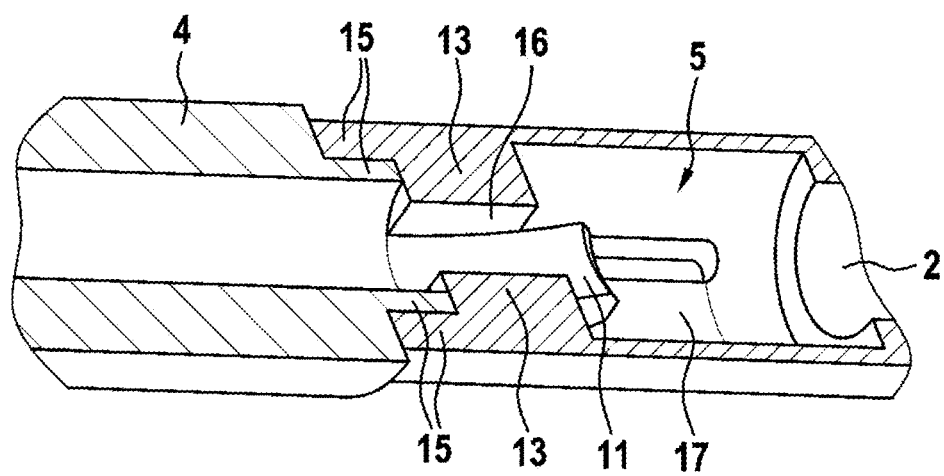
FIG. 6 is a longitudinal sectional view according to FIG. 4 rotated by 90°.

To form the undercuts 12 forming the latching receptacles 10, a radially inwardly projecting shoulder 13 that reduces the diameter of the rod 2 is formed at the distal end 3 of the rod 2 on the inside of the rod 2, as can be seen in FIG. 4-6. The proximal end of this shoulder 13 forms the undercut 12 for positioning the latching hook 9.

In the embodiment of the mechanical latching connection shown in FIG. 3-5, two resilient spring tongues 11 provided with latching hooks 9 and two corresponding latching receptacles 10 configured as undercuts 12 are provided for the latching hooks 9, wherein the latching hooks 9 and latching receptacles 10 are each arranged offset by 180° relative to one another over the circumference of the tool carrier 4 or the rod 2.

The use of two or more latching hooks 9 and correspondingly two or more corresponding latching receptacles 10 ensures, on the one hand, uniform and tilt-free mounting of the coupled components and, on the other hand, reduces the risk of accidental release of the latch, because all latches would have to be released simultaneously.

Starting from the disconnected position of the two components shown in FIG. 3, the tool carrier 4 is coupled to the distal end 3 of the rod 2 by pushing the tool carrier 4 and the rod 2 toward each other in the direction of the longitudinal axis 14 of the rod 2.

When the latching hooks 9 of the tool carrier 4 run against the distal end 3 of the rod 2 and in particular against the radially inwardly projecting shoulder 13 in the distal end 3 of the rod 2, the resilient spring tongues 11 are bent radially inward, so that the latching hooks 9 slide along the shoulder 13 until the latching hooks 9 at the end of the shoulder 13 snap into the latching abutment on the undercuts 12 of the latching receptacles 10 due to the resilient spring-back of the spring tongues 11, as is shown in FIG. 4.

In order to facilitate the joining of the components to be coupled together and to align them in the correct position relative to one another, guide pins 15 are formed on the end sides facing one another of the components to be joined together in order to place the components in the correct position relative to one another, as is shown in particular in FIG. 6.

As can also be seen from FIG. 6, a guide groove 16 for the spring tongues 11 of the latching hooks 9 is formed in the shoulder 13, so that the spring tongues 11 in the latched state positively abut against the shoulder 13 of the latching receptacles 10 so as to produce an anti-rotation lock.

The latch between the latching hooks 9 and the undercuts 12 is preferably released without tools by applying a radially acting compressive force D to the latching connection.

In the embodiment shown in FIGS. 2 to 6, a cut-free spring tongue 17 is formed in the rod 2 in the region of each latch, which can be pressed radially inward to release the latching connections by applying the radially acting compressive force D, as shown in FIG. 5.

When the spring tongues 17 are pressed down, the spring tongues 17 abut against the latching hooks 9 engaging behind the undercuts 12. Due to the mounting of the latching hooks 9 at the end of the resilient spring tongues 11, the latching hooks 9 together with the spring tongues 11 are also pressed radially inward when a radial compressive force D is exerted on the cut-free spring tongues 17 in the rod 2.

By pressing the latching hooks 9 radially inward in relation to the rod 2, the latching hooks 9 disengage from the undercuts 12 and thus release the first fastening mechanism 5 again, so that the tool carrier 4 and the rod 2 can be pulled apart in opposite directions to separate the two components.

The advantage of a mechanical latching connection configured in this way is that these latching connections are easy to manufacture and easy to handle, while ensuring a secure connection between the interconnected components.

As an alternative to forming the cut-free spring tongue 17 in the rod 2 for releasing the latch, it is also possible to make the rod 2 elastically deformable in the region of the latch, so that when the radial compressive force D is applied, the rod 2 can be pressed radially inward in order to release the latching connection by running against the latching hooks 9.

In the embodiment of the mechanical latching connection shown in FIGS. 2 to 6 configured as a plug-in connection that can be executed in the longitudinal direction of the rod 2.

According to an alternative embodiment not shown, however, it is also possible to design the mechanical latching connection as a rotary plug-in connection, wherein the two components are latched together as described above, but when the two components are joined together, the two components are rotated relative to each other in addition to the axial movement.

Figure 7:
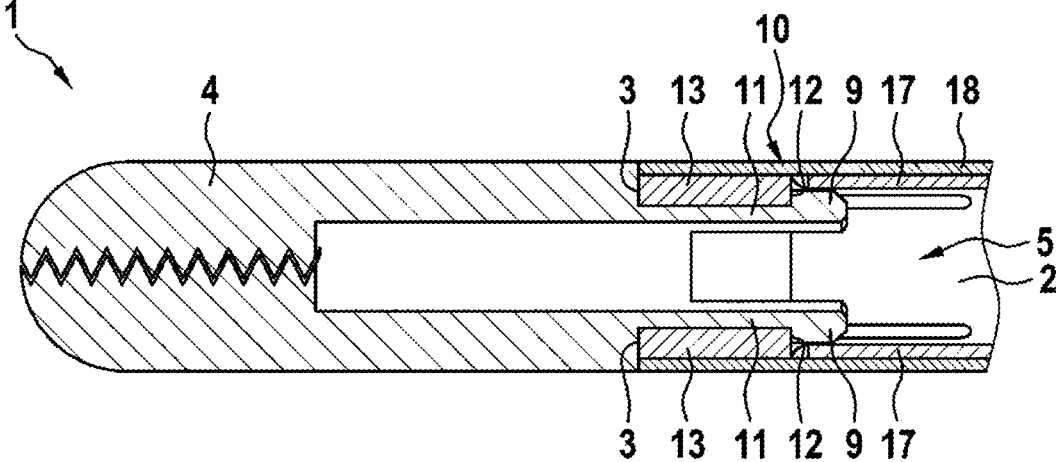
FIG. 7 is a schematic longitudinal sectional view according to FIG. 4, but showing the rod with a tubular cover.

As can be seen from FIG. 7, the embodiment described above can also be used when the medical instrument 1 is configured as an HF instrument if the cut-free spring tongue 17 is covered with a tubular cover 18 for insulation purposes.

Figure 8:
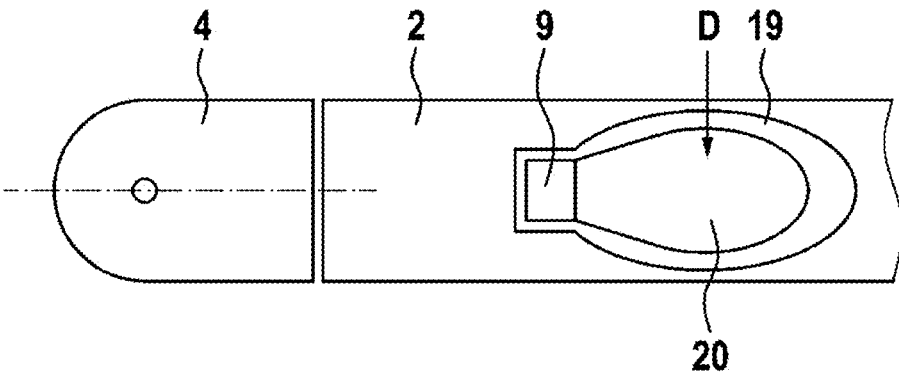
FIG. 8 is a schematic longitudinal sectional view through the tool carrier and the distal end of the rod, illustrating a second embodiment according to the invention.

The second embodiment shown in FIG. 8 for forming the mechanical latching connection differs from the embodiment shown in FIGS. 2 to 6 in that, instead of the cut-free spring tongues 17, openings 19 are formed in the rod 2 in the region of the latches via which the user of the medical instrument 1 has direct access to the latching hooks 9 in order to press them inward into the rod 2 by applying a radial compressive force D until they are out of engagement with the undercuts 12. In the embodiment shown in FIG. 8, a tongue 20 extending in the direction of the longitudinal axis 14 of the rod 2 is formed on the latching hooks 9, which makes it easier to press in the latching hooks 9.

Figure 9:
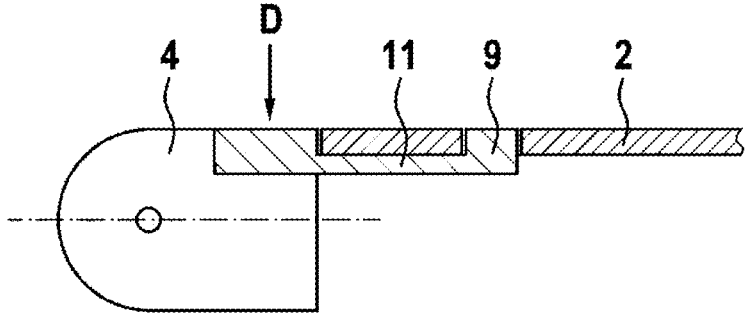
FIG. 9 is a schematic longitudinal sectional view according to FIG. 8, but showing a third embodiment according to the invention.

In the third embodiment shown in FIG. 9, the latch is released by applying the radial compressive force D not to the latch in the region of the latching hooks 9, but to the distal end of the resilient spring tongues 11 remote from the latching hooks, for which purpose the material of the tool carrier 4 is configured to be elastically deformable in the region of the mounting of the spring tongues 11. When the tool carrier is pressed in, the spring tongues 11 together with the latching hooks 9 on the end are bent radially inward, so that the latching hooks 9 disengage from the undercuts 12 and the two components can be separated again by pulling them apart.

Figure 10:
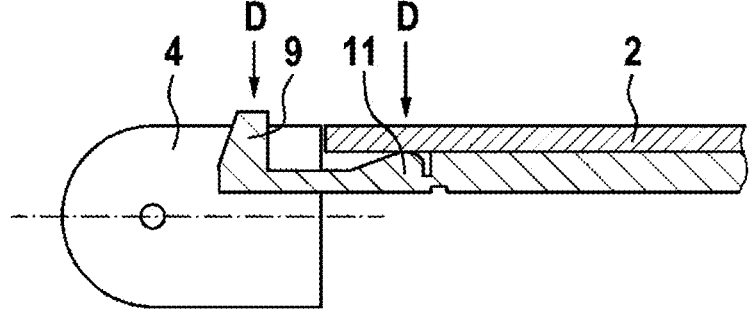
FIG. 10 is a schematic longitudinal sectional view according to FIG. 8, but showing a fourth embodiment according to the invention.

The fourth embodiment shown in FIG. 10 for forming the mechanical latching connection shows that the arrangement of latching hook 9 and latching receptacle 10 on the components to be coupled together can also be reversed.

Whereas in the previously illustrated and described embodiments the spring tongues 11 with the latching hooks 9 were always arranged on the tool carrier 4 and the undercuts 12 forming the latching receptacles 10 were always arranged on the rod 2, FIG. 10 shows an embodiment in which the spring tongues 11 provided with the end-side latching hooks 9 are formed on the rod 2 and the latching receptacles 10 are formed on the tool carrier 4.

In this embodiment, the undercuts 12 forming the latching receptacles 10 are formed by a recess 21 in the tool carrier 4 into which the latching hooks 9 engage in the latched position, as can be seen in FIG. 10.

In the embodiment shown in FIG. 10, the latch can be released by exerting the radial compressive force D either directly on the latching hooks 9 mounted in the recesses 21 of the tool carrier 4, or on the end of the resilient spring tongues 11 remote from the latching hook, for which purpose the material of the distal end 3 of the rod 2 is configured to be elastically deformable in the region of the mounting of the spring tongues 11.

The arrangement of the latching hooks 9 and latching receptacles 10 shown in FIG. 10 can also be transferred to all embodiments of the mechanical latching connections shown above in FIGS. 2 to 9.

The mechanical latching connections configured as described above are characterized by the fact that these rod connections are easy to handle during production and assembly while ensuring a secure hold of the coupled components.

While specific embodiments of the invention have been shown and described in detail to illustrate the application of the principles of the invention, it will be understood that the invention may be embodied otherwise without departing from such principles.

LIST OF REFERENCE CHARACTERS 1 medical instrument
2 rod
3 distal end (rod)
4 tool carrier
5 first fastening mechanism
6 proximal end (rod)
7 second fastening mechanism
8 operating unit 9 latching hook
10 latching receptacle
11 spring tongue
12 undercut
13 shoulder
14 longitudinal axis
15 guide pin
16 guide groove
17 spring tongue
18 tubular cover
19 opening
20 tongue
21 recess
D compressive force
The invention claimed is:

1. A medical instrument comprising:
a hollow rod;
a first fastening mechanism; and
a second fastening mechanism, wherein at a distal end of the hollow rod, a tool carrier is securable by means of the first fastening mechanism, and at a proximal end of the hollow rod, an operating unit is securable by means of the second fastening mechanism, and wherein the first fastening mechanism for connecting the tool carrier to the distal end of the rod is configured as a mechanical latching connection having at least one resilient element,
wherein the hollow rod and the tool carrier comprise components to be connected to one another and the mechanical latching connection of the first fastening mechanism is comprised of at least one latching hook, formed on one of the components of the hollow rod or the tool carrier, and at least one corresponding latching receptacle, formed on the other component of the hollow rod or the tool carrier, for the at least one latching hook,
wherein a cut-free spring tongue is formed on the other component of the hollow rod or the tool carrier with the at least one latching receptacle in a region of the latch, which the spring tongue is configured to be pressed radially inward to release the latching connection.

2. The medical instrument according to claim 1, wherein the second fastening mechanism for connecting the proximal end of the rod to the operating unit is also configured as a mechanical latching connection having at least one resilient element.

3. The medical instrument according to claim 2, wherein:
wherein the hollow rod and the operating unit comprise components to be connected to one another, the mechanical latching connection of the second fastening mechanism is comprised of at least one latching hook formed on one of the components of the hollow rod or the operating unit to be connected to one another and at least one corresponding latching receptacle formed on the other component of the hollow rod or the operating unit, for the at least one latching hook of the second fastening mechanism.

4. The medical instrument according to claim 3, wherein the at least one latching hook of the first or the second fastening mechanisms is arranged at a free end of a resilient spring tongue.

5. The medical instrument according to claim 4, wherein the resilient spring tongue of the at least one latching hook of the first or second fastening mechanisms positively abuts against a shoulder of the at least one latching receptacle of the first or second fastening mechanisms so as to produce an anti-rotation lock.

6. The medical instrument according to claim 3, wherein the at least one latching receptacle of the first or second fastening mechanisms is configured as an undercut.

7. The medical instrument according to claim 3, wherein the at least one latching hook of the first or second fastening mechanisms comprises a plurality of latching hooks and the at least one latching receptacle of the first or second fastening mechanisms comprises a plurality of latching receptacles, wherein the plurality of latching hooks and latching receptacles of the first or second fastening mechanisms are arranged distributed over a circumference of their respective components to be connected to one another.

8. The medical instrument according to claim 3, wherein a second cut-free spring tongue is formed on the component of the hollow rod or the operating unit with the at least one latching receptacle of the second fastening mechanism in a region of the latch, which the second spring tongue is configured to be pressed radially inward to release the latching connection.

9. The medical instrument according to claim 1, wherein the at least one latching hook is arranged at a free end of a resilient spring tongue.

10. The medical instrument according to claim 9, wherein the resilient spring tongue of the at least one latching hook positively abuts against a shoulder of the at least one latching receptacle so as to produce an anti-rotation lock.

11. The medical instrument according to claim 1, wherein the at least one latching receptacle is configured as an undercut.

12. The medical instrument according to claim 1, wherein the at least one latching hook comprises a plurality of latching hooks and the at least one latching receptacle comprises a plurality of latching receptacles, wherein the plurality of latching hooks and latching receptacles are arranged distributed over a circumference of the their respective components to be connected to one another.

13. The medical instrument according to claim 1, wherein the mechanical latching connection is configured to be released by applying a radially acting compressive force (D).

14. The medical instrument according to claim 1, wherein the mechanical latching connection is configured as a plug-in connection that is configured to be executed in a longitudinal direction of the rod.

15. The medical instrument according to claim 1, wherein the mechanical latching connection is configured as a rotary plug-in connection.

16. The medical instrument according to claim 1, wherein the cut-free spring tongue is configured to be covered with a tubular cover.

17. The medical instrument according to claim 1, wherein the latch of the first fastening mechanism is releasable by transferring a tool of the tool carrier into an unlocking position.

18. The medical instrument according to claim 1, wherein guide pins are formed on end sides facing one another of the components to be connected to one another in order to place the components in the exact position relative to one another.

19. A medical instrument comprising:
a hollow rod;
a first fastening mechanism; and
a second fastening mechanism, wherein at a distal end of the hollow rod, a tool carrier is securable by means of the first fastening mechanism, and at a proximal end of the hollow rod, an operating unit is securable by means of the second fastening mechanism, and wherein the first fastening mechanism for connecting the tool carrier to the distal end of the rod is configured as a mechanical latching connection having at least one resilient element, wherein the second fastening mechanism for connecting the proximal end of the rod to the operating unit is also configured as a mechanical latching connection having at least one resilient element, wherein the hollow rod and the tool carrier comprise components to be connected to one another, wherein the mechanical latching connection of the first fastening mechanism is comprised of at least one latching hook formed on one of the components of the hollow rod or the tool carrier to be connected to one another and at least one corresponding latching receptacle formed on the other component of the hollow rod or the tool carrier, for the at least one latching hook, wherein the hollow rod and the operating unit comprise components to be connected to one another, the mechanical latching connection of the second fastening mechanism is comprised of at least one latching hook formed on one of the components of the hollow rod or the operating unit to be connected to one another and at least one corresponding latching receptacle formed on the other component of the hollow rod or the operating unit, for the at least one latching hook of the second fastening mechanism, and wherein a cut-free spring tongue is formed on the component with the at least one latching receptacle of the first or second fastening mechanisms in a region of the latch, which the spring tongue is configured to be pressed radially inward to release the latching connection.

\* \* \* \* \*